United States Patent [19]

Kent

[11] Patent Number: 5,229,726
[45] Date of Patent: Jul. 20, 1993

[54] PORTABLE DEVICE FOR USE IN THE MEASUREMENT OF A COMPONENT CONTENT OF A MATERIAL

[75] Inventor: Michael Kent, Aberdeenshire, Scotland

[73] Assignee: The Secretary of State for Minister of Agriculture Fisheries and Food In Her Britannic Majesty's Government of the united Kingdom of Great Britain and Northern Ireland, London, England

[21] Appl. No.: 778,195

[22] PCT Filed: Jul. 2, 1990

[86] PCT No.: PCT/GB90/01013

§ 371 Date: Jan. 3, 1992

§ 102(e) Date: Jan. 3, 1992

[87] PCT Pub. No.: WO91/00512

PCT Pub. Date: Jan. 10, 1991

[30] Foreign Application Priority Data

Jul. 4, 1989 [GB] United Kingdom ............... 8915323

[51] Int. Cl.⁵ .......................................... G01N 22/00
[52] U.S. Cl. .................................. 324/632; 324/640; 324/639; 324/647; 324/608
[58] Field of Search ............... 324/632, 639, 640, 647, 324/637, 608

[56] References Cited

U.S. PATENT DOCUMENTS

| | | | |
|---|---|---|---|
| 3,581,197 | 5/1971 | Morey, Jr. et al. | 324/61 |
| 4,104,584 | 8/1978 | Miyai et al. | 324/58.5 R |
| 4,674,325 | 6/1987 | Kiyobe et al. | 73/73 |
| 5,103,181 | 4/1992 | Gaisford et al. | 324/637 |

FOREIGN PATENT DOCUMENTS

| | | |
|---|---|---|
| 1354474 | 5/1974 | United Kingdom . |
| 2112148A | 7/1983 | United Kingdom . |
| 2202947A | 10/1988 | United Kingdom . |

OTHER PUBLICATIONS

Journal of Food Science, vol. 39, Dec. 1974, T. Ohlsson et al: "Dielectric Properties of Model Meat Emulsions at 900 and 2800 MHz In Relation (con't) to Their Composition".

Primary Examiner—Kenneth A. Wieder
Assistant Examiner—Jose M. Solis
Attorney, Agent, or Firm—Nixon & Vanderhye

[57] ABSTRACT

A portable device for use in the measurement of the dielectric properties of materials such as fish includes: a microwave circuit comprising a microwave source (10) connected via an isolator (12) to a directional coupler (14), a first output (16) of which is connected to a reference detector (18) and a first pre-amplifier (28) and a second output (20) of which is connected via an attenuator (22) to a sensor (24), an output of which is connected to a signal detector (26) and a second pre-amplifier (30); and further including two amplifiers (32, 34) into which outputs of the first (28) and second (30) pre-amplifiers are connected and a logarithmic/ratio device (38) which provides an output proportional to the logarithm of the ratio of outputs from the two amplifiers (32, 34), wherein an output from the logarithmic/ratio device (38) is calibrated to provide the content of a particular constituent of the material under test.

28 Claims, 5 Drawing Sheets

PORTABLE DEVICE FOR USE IN THE MEASUREMENT OF A COMPONENT CONTENT OF A MATERIAL

BACKGROUND OF THE INVENTION

1. Field of the Invention

This invention relates to a portable device for use in the measurement of a component content of a material, particularly the water content of a material and water and fat content of whole fish, using the dielectric properties of the component. The rapid determination of water and fat content of products is a prevailing problem in the fish industry, since these contents affect various processing operations of the fish, for example, when smoking the fish. In this respect, manufacturers need to determine the fat content of fish so as to assess final product quality—a medium fat content indicates a better quality than either low or high fat content. For similar reasons fish farmers need to assess the fat content of live fish before selling to customers.

2. Discussion of Prior Art

In whole fish flesh, such as herring and other pelagic species, the problem is to a certain extent simplified by the fact that a linear relationship exists between the fraction of water and that of fat (Iles and Wood, 1965) so that the measurement of one serves to determine the other within the limit of this relationship. Such a relationship arises from the physiological need of the fish to maintain a slightly negative buoyancy even while the fat content, which is of low density, tends to creat the opposite effect. Variation in fat content arises from seasonal effects of food availability and breeding cycle.

Tests do exist for the measurement of water and fat content of fish but the main disadvantage of these tests is that they are destructive in that the fat must firstly be extracted from the fish, then after mixing this with a solvent, chemical analysis is used to determine the fat and water contents. These current methods also have the added disadvantage of being very time-consuming, and cannot be used on whole or live fish. Nuclear Magnetic Resonance (NMR) may also be used but is expensive and bulky.

It is known (Mudgett et al (1974), J Food Sci, 39, 632–635) that in the microwave frequency region the dielectric properties of materials are dominated by those of water especially if the water fraction is large. Thus the attenuation of microwave energy by a material provides a measure of the moisture content of the material. It is also known (Ohlsson et al (1974) J Food Sci, 39, 1153–1156) that both the fat and water contents of meat emulsions could be determined from various dielectric measurements in the microwave range. However, in those data no correlation existed between the fat and water content.

It is further known (Kent 1989) that there is a good correlation between the water content of the fish and the real part of the dielectric permittivity at all frequencies in the microwave range. There exists many methods for the measurement of the dielectric properties of materials, one such method being the subject of UK Patent No 1354474. This method depends on the dielectric sensitive properties of a form of transmission line known as a microstrip or stripline sensor.

However, those known methods of the measurement of the dielectric properties of materials all use apparatus which are large and bulky, inconvenient and not portable.

There is therefore a need for a portable device for the measurement of the dielectric properties of materials, in particular the water content of materials and the fat and water content of whole or live fish which has the advantages of being both convenient and easy to use.

SUMMARY OF THE INVENTION

According to the present invention, a portable device for use in the measurement of a component content of a particular material using the dielectric properties of the component is characterised in including; a microwave circuit comprising a microwave source connected via an isolator to a directional coupler, a first output of which is connected to a reference detector and a first pre-amplifier and a second output of which is connected via an attenuator to a sensor, of the type wherein a signal passing therethrough is affected by an adjacent dielectric material, an output of which is connected to a signal detector and a second pre-amplifier; and further including first and second amplifiers into which outputs of the first and second pre-amplifiers are respectively connected, and a logarithmic/ratio device which provides an output proportional to the logarithm of the ratio of outputs from the first and second amplifiers, wherein the output of the logarithmic/ratio device is calibrated to provide the content of a particular constituent of the material under test.

The microwave circuit is housed in a hand held probe, whilst the rest of the device plus batteries and switches are in a separate unit connected to the probe. Thus the device is portable and easy to use. For laboratory use, however, the device may be modified to run on an available main electrical supply.

The output of the logarithmic/ratio device is preferably fed directly to a digital voltmeter in the hand held part of the instrument. The instrument is pre-calibrated to give a reading of the content of a particular constituent of the material under test. This is preferably water, but could also be fat, in the case of fish.

The sensor used in the device may take a number of different forms. Preferably a microstrip or stripline sensor is used as disclosed in UK Patent No 1354474. Alternatively a directional coupler or a circulator could be used, feeding an open-ended coaxial line in a reflectomer mode.

The microwave source may be any suitable low-current drain microwave source, but is preferably a Gunn diode. The microwave circuit may be made up of discrete components; alternatively it may be made from stripline with all components on one substrate.

The device preferably has a microprocessor to perform a number of operations, for example storing calibration equations and providing a facility for averaging a predetermined number of readings. This latter function would allow, for example, the mean fat content of a batch of fish to be estimated.

BRIEF DESCRIPTION OF THE DRAWINGS

The present invention will now be described by way of example only, with reference to the accompanying diagrammatic drawings in which.

DETAILED DISCUSSION OF PREFERRED EMBODIMENTS

Figure 1:
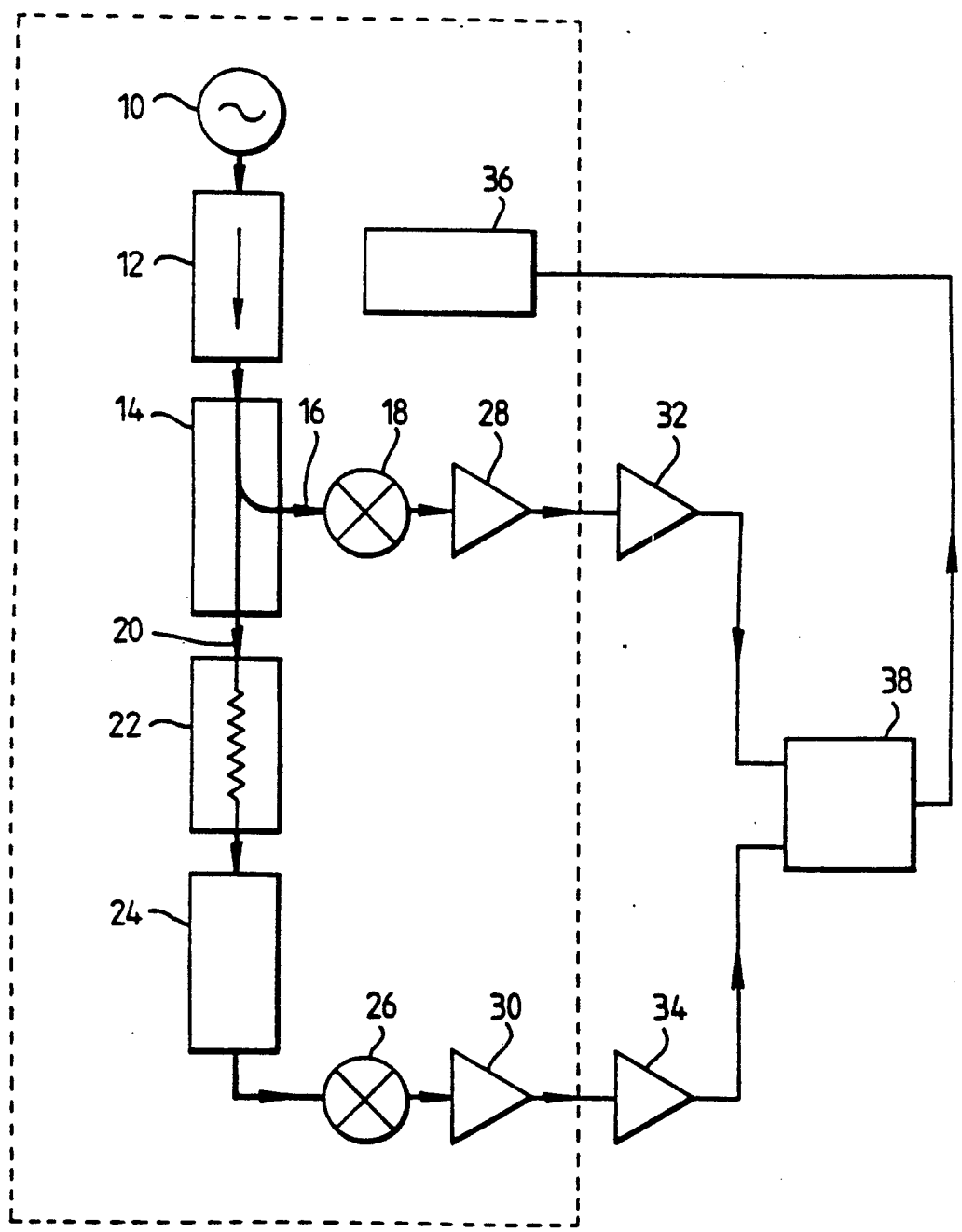
FIG. 1 is a block circuit diagram of a device according to the present invention.
Figure 2:
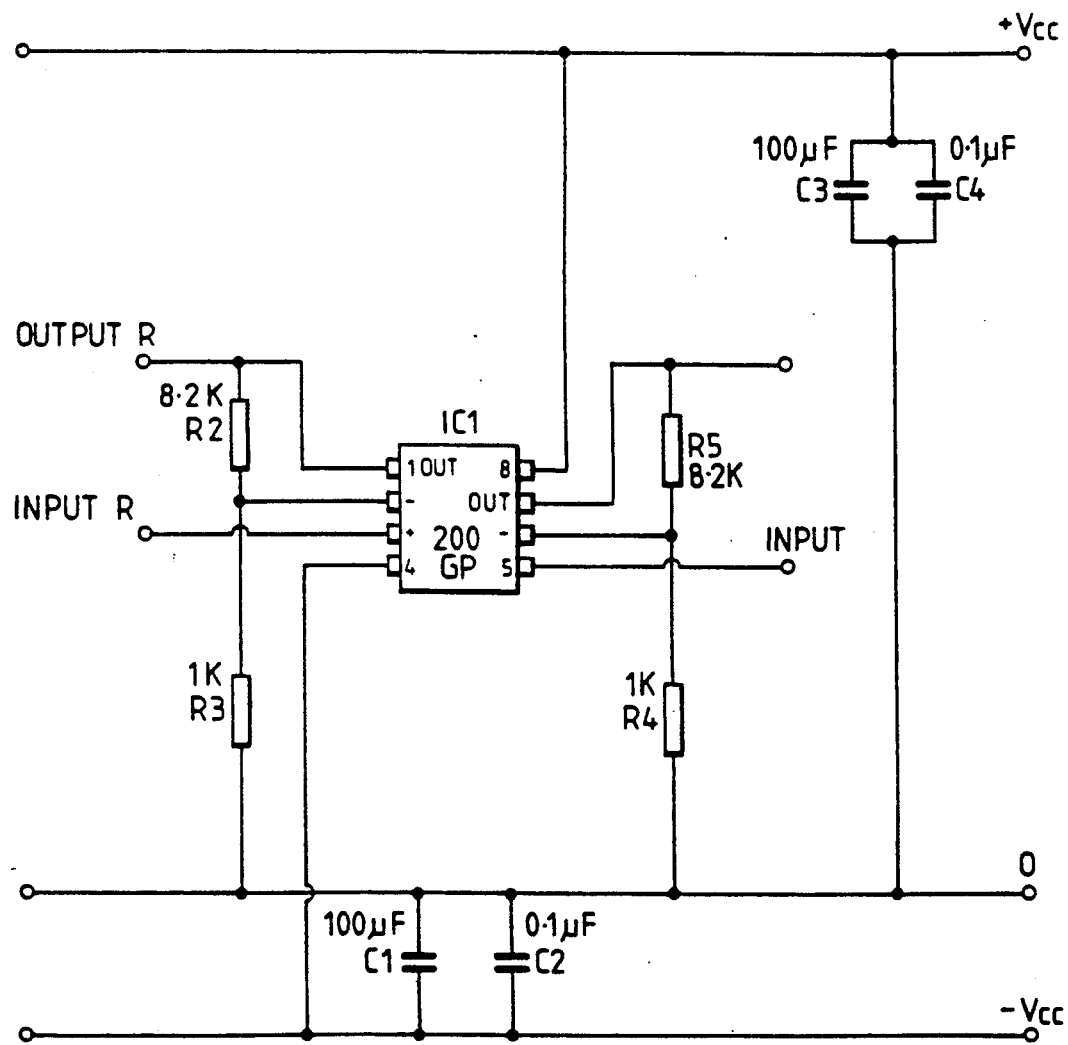
FIG. 2 is a circuit diagram of a pre-amplifier of FIG. 1.
Figure 3:
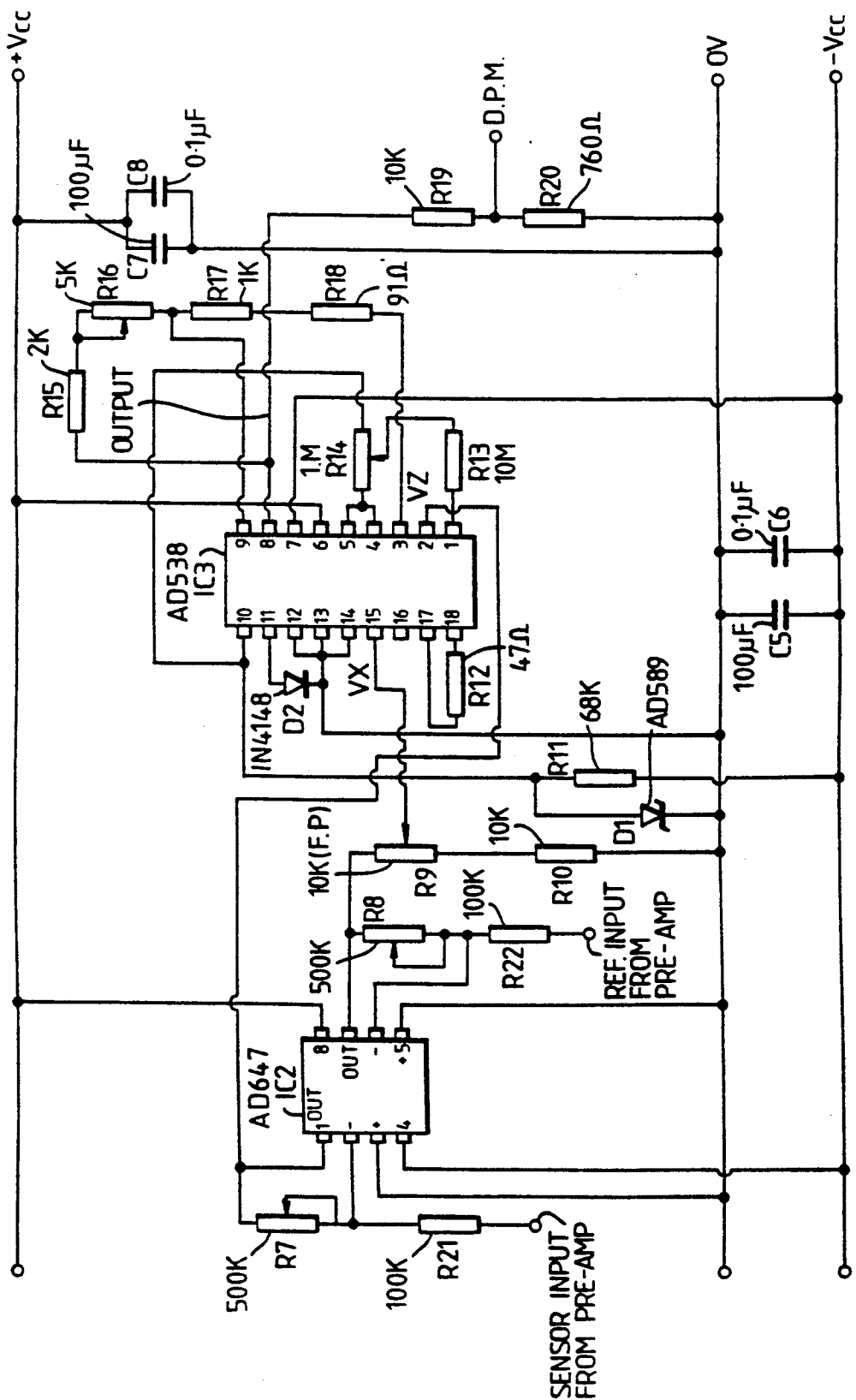
FIG. 3 is a circuit diagram of the logarithmic/ratio amplifier of FIG. 1.

As shown in FIG. 1 a device for use in the measurement of a component content of materials using the dielectric properties of the materials has a microwave circuit which measures the insertion loss or attenuation of power comprising of a microwave source 10, preferably a Gunn diode, connected via an isolator 12 to a directional coupler 14. One output 16 of the directional coupler 14 is connected to a reference detector 18 and the other output 20 is connected via an attenuator 22 to a stripline sensor 24, the output of which is connected to a signal detector 26. Outputs of the reference detector 18 and the signal detector 26 are connected to first and second low gain voltage follower type pre-amplifiers 28 and 30 respectively (circuit diagram at FIG. 2). Each of these are connected to further amplifiers 32 and 34, respectively. The output of these are then connected to a logarithmic ratio amplifier 38 (circuit diagram at FIG. 3). The output of the logarithmic/ratio device 38 is fed directly to a digital voltmeter 36. The boxed area of FIG. 1 is that part of the device housed in a hand held probe 100. The rest plus batteries and switch (not shown) are in a separate unit 101 connected to the probe by multicore cable.

Figure 4:
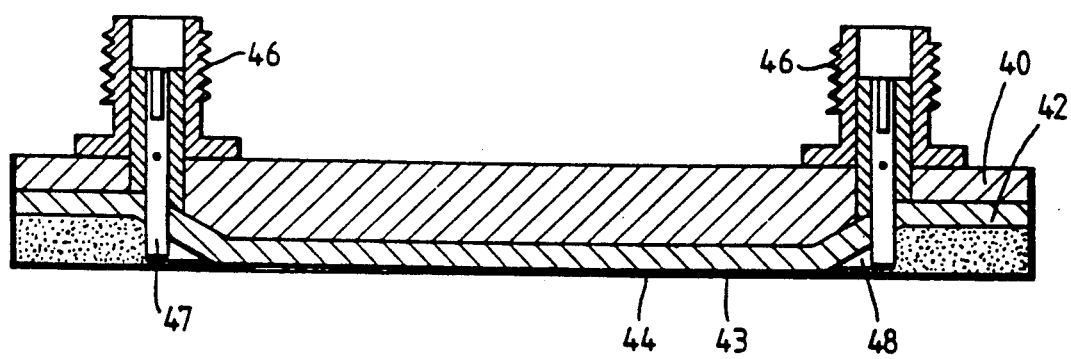
FIG. 4 is a side view in section of the stripline sensor used in the present invention.

The stripline sensor 24 is shown in FIG. 4 and consists of a piece of microstrip having a base plate 40, a substrate 42 and a strip conductor 43. A protective layer 44 of preferably polytetrafluoroethylene (ptfe) material is fixed directly over the strip conductor 43. The substrate 42, is preferably made of a ptfe and ceramic mixture with a permittivity of 10 and very low loss. The sensor is shown with transitions from stripline to coaxial line 46, the transition being made by feeding the centre conductor 47 of a coaxial line jack type connector 46 through the substrate 42 and soldering to the surface of the strip conductor 43 at 48. The stripline sensor allows a flat surface 50 to be presented to the material under test.

Figure 5:
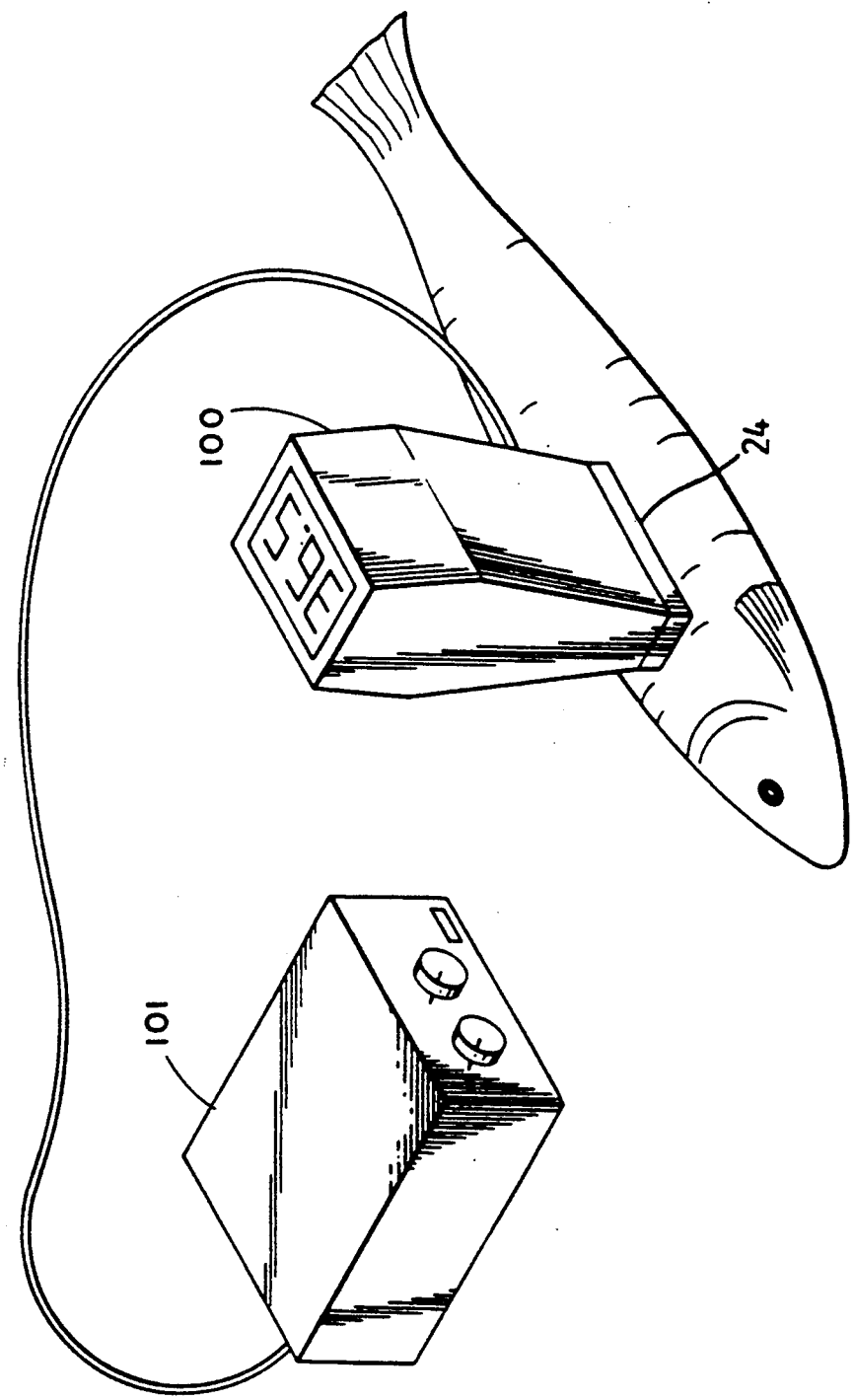
FIG. 5 shows the device according to the present invention being used to test the dielectric properties of whole fish.

FIG. 5 shows the device in operation. In use, the sensor 24 in the hand held probe 100 is placed directly on top of the material to be tested and the Gunn diode 10 is switched on. Power from the Gunn diode 10 is fed via the isolator 12 to the 10 dB directional coupler 14. The purpose of the isolator is to prevent any reflection power from interfering with the operation of the Gunn diode. The directional coupler feeds 10 dB of the power to the reference detector 18. The major part of the power is fed through the 10 dB attenuator 22 to the stripline sensor 24. The attenuator 22 reduces the power to a level comparable with that in the reference arm. This level is also low enough to ensure square law operation of the detectors given the input power of a few milliwatts. It also reduces the effect on both the Gunn-diode 10 and the directional coupler 14 of reflected power from the various mismatches in the sensor. Apart from the obvious mismatch of the sensor impedance there are also reflections from the coaxial-to-stripline transitions which are difficult to eliminate entirely. After passing through the sensor 24 the remaining power is detected by another signal detector 26.

The Gunn diode 10 oscillates at 10 $GH_z$ with a supply voltage of $-7.5$ V and delivers about 10 mW of power. The current drawn from the power supply for this is around 200 mA so in order to conserve battery energy and life the Gunn diode 10 is only switched on for the duration of the measurement. Since it never achieves thermal equlibrium it is therefore most probable that both the frequency and the power output are to some extent time dependent. This is where the value of the reference system 18 is demonstrated since the ratio of the power in the signal detector to that in the reference detector is always measured. Thus variations in power level during this transient operation are not important. The frequency shift that takes place is small enough to render negligible any frequency dependent changes that might occur in the various components. All Components have fairly broadband characteristics (8–12 $GH_z$). although the system described operates in this particular frequency range (X-band) it can be constructed to function at any microwave frequency. For some applications it might in fact be better to make the measurements at 1–2 $GH_z$.

The output from the reference detector 18 is about 100 mV while that from the signal detector 26 ranges from 100 $\mu$V up to 100 mV depending on the loss in the sensor 24. These two dc signals are each fed to the low gain voltage follower type pre-amplifiers 28,30. The amplified signals are then fed through a further stage of amplification 32, 34 to the logarithmic/ratio device 38 which provides an output proportional to the logarithm of the ratio of the two signals. This signal is proportional to the decibel ratio of the signals and is calibrated against the content of the desired constituent of the material. In this case, the constituent would be the fat or water content of the fish. This signal is fed to a digital voltmeter 36 in the hand held part of the probe. This will display the content of the desired constituent. The device is pre-calibrated to measure a particular constituent. For example, for calibration to measure the fat content of herring the following equation relates the microwave attenuation A and fat content F as:

$$\log_e(F) = a - bA$$

where a = 5.05
and b = 0.166

The device also preferably contains a microprocessor (not shown) to perform a number of operations, such as storing calibration equations and providing a facility for averaging a predetermined number of readings. This latter function allows, for example, the mean fat content of a batch of fish to be estimated.

The device is not restricted for use with fish alone. Indeed, any material may be tested for water content including liquids such as cement and slurries. Also, the constituent measured is not restricted to water but also fat in the case of fish, as mentioned above, because of the linear relationship between fat and water content of fish. Additionally, the amount can be measured of a particular constituent in any material whose dielectric properties are affected by that constituent.

Hence a portable device has been described for the measurement of the component content of a material which can be mains or battery driven, is convenient and easy to use, in particular for testing whole or live fish for fat content.

What is claimed is:

1. A portable device for the measurement of a component content of a material using the dielectric properties of said material, said device comprising:
   a microwave source means for producing microwave radiation at an output;
   a directional coupler means, responsive to said microwave radiation, for providing microwave radiation at first and second outputs;
   a reference detector, responsive to microwave radiation from said first output, for providing a voltage output indicative of the microwave radiation from said first output;
   sensor means, responsive to microwave radiation from said second output and locatable adjacent said material, for varying transmission of microwave radiation from said second output to a sensor means output in response to dielectric properties of said material;
   a signal detector, responsive to microwave radiation from said sensor means output, for providing a voltage output indicative of the microwave radiation from said sensor means output;
   logarithmic ratio amplifier means, responsive to said reference detector output and said signal detector output, for providing an output indicative of the ratio of one of said reference detector output and said signal detector output to the other of said reference detector output and said signal detector output; and
   indicator means, responsive to the output of said logarithmic ratio amplifier means and calibrated to indicate component content, for indicating component content of said material.

2. A portable device as claimed in claim 1, wherein said sensor means is housed in a hand-held probe.

3. A portable device as claimed in claim 1, wherein the device further includes batteries on which the device runs.

4. A portable device as claimed in claim 1, wherein the device further includes a main electrical supply for powering the device.

5. A portable device as claimed in claim 2, wherein the output of the logarithmic ratio amplifier means is fed directly to a digital voltmeter housed in the hand-held probe.

6. A portable device as claimed in claim 1, wherein said sensor means is a stripline sensor.

7. A portable device as claimed in claim 1, wherein the sensor means is a directional coupler feeding an open-ended coaxial line in a reflectometer mode.

8. A portable device as claimed in claim 1, wherein the sensor means is a circulator feeding an open-ended coaxial line in a reflectometer mode.

9. A portable device as claimed in claim 1, wherein said microwave source means is a Gunn diode.

10. A portable device as claimed in claim 1, wherein said microwave source means, said directional coupler means, said reference detector, said sensor means and said signal detector comprise a microwave circuit, said microwave circuit is made from stripline with all components on one substrate.

11. A portable device as claimed in claim 1, wherein the device further includes a microprocessor responsive to said logarithmic ratio amplifier means.

12. A portable device as claimed in claim 11 wherein the microprocessor includes means for storing calibration equations.

13. A portable device as claimed in claim 11 wherein the microprocessor includes means for averaging a predetermined number of readings.

14. A portable device as claimed in claim 1, wherein the component content is water.

15. A portable device as claimed in claim 1, wherein the fat content of fish is the component content.

16. A portable device for the measurement of a component content of a material using the dielectric properties of said material, said device comprising:
    a microwave source means for producing radiation at an output;
    an isolator means, responsive to said microwave radiation from said microwave radiation source means, for providing microwave radiation at an output and for isolating said microwave radiation source means from any reflected microwave radiation;
    a directional coupler means, responsive to said microwave radiation from said isolation means output, for providing microwave radiation at first and second outputs;
    a reference detector, responsive to microwave radiation from said first output, for providing a voltage output indicative of the microwave radiation from said first output;
    a reference amplifier for amplifying said reference detector voltage output and for providing a first amplified voltage output;
    an attenuator means, responsive to said directional coupler means second output, for providing attenuated microwave radiation;
    stripline sensor means, responsive to microwave radiation from said attenuator means and locatable adjacent said material, for varying transmission of microwave radiation from said second output in response to dielectric properties of said material;
    a signal detector, responsive to microwave radiation from said stripline sensor means, for providing a voltage output indicative of the microwave radiation from said stripline sensor means;
    a signal amplifier for amplifying said signal detector voltage output and for providing a second amplified voltage output;
    logarithmic ratio amplifier means, responsive to said first amplified output and said second amplified output, for providing an output indicative of the ratio of one of said reference detector output and said signal detector output to the other of said reference detector output and said signal detector output; and
    indicator means, responsive to the output of said logarithmic ratio amplifier means and calibrated to indicate component content, for indicating component content of said material.

17. A portable device for the measurement of a component content of a material according to claim 1, further including:
    an isolator means, responsive to said microwave radiation from said microwave radiation source means, for transmitting said microwave radiation to said directional coupler means and for isolating said microwave radiation source means from any reflected microwave radiation.

18. A portable device for the measurement of a component content of a material according to claim 1, further including:
    a reference amplifier for amplifying said reference detector voltage output and applying a first amplified voltage output to said logarithmic ratio amplifier means; and a signal amplifier for amplifying said signal detector voltage output and applying a second amplified voltage output to said logarithmic ratio amplifier means.

19. A portable device for the measurement of a component content of a material according to claim 18,
wherein said reference amplifier comprises:
a first preamplifier for providing a pre-amplified reference detector voltage output; and
a first amplifier, responsive to said pre-amplified reference detector voltage output, for providing an amplified reference detector voltage output to said logarithmic ratio amplifier means;
wherein said signal amplifier comprises:
a second preamplifier for providing a pre-amplified signal detector voltage output; and
a second amplifier, responsive to said pre-amplified signal detector voltage output, for providing an amplified signal detector voltage output to said logarithmic ratio amplifier means.

20. A portable device for the measurement of a component content of a material according to claim 1, further including an attenuator means, responsive to said directional coupler means, for providing attenuated microwave radiation to said sensor means.

21. A portable device for the measurement of a component content of a material according to claim 20, wherein said attenuator means comprises a means for reducing microwave radiation power from said second output of said directional coupler means to a level substantially equal to microwave radiation power applied to said reference detector from said first output of said directional coupler means.

22. A portable device for the measurement of a component content of a material according to claim 1, wherein said indicator means is comprised of a digital voltmeter.

23. A portable device for the measurement of a component content of a material using the dielectric properties of said material, said device comprising:
a microwave source means for producing microwave radiation at an output;
a directional coupler means, responsive to said microwave radiation, for providing microwave radiation at first and second outputs;
a reference detector, responsive to microwave radiation from said first output, for providing an output indicative of a characteristic of the microwave radiation from said first output;
sensor means, responsive to microwave radiation from said second output and locatable adjacent said material, for varying said characteristic of microwave radiation from said second output to a sensor means output in response to dielectric properties of said material;
a signal detector, responsive to microwave radiation from said sensor means output, for providing a voltage output indicative of said characteristic of the microwave radiation from said sensor means output;
means, responsive to said reference detector output and said signal detector output, for providing an output indicative of the ratio of one of said reference detector output and said signal detector output to the other of said reference detector output and said signal detector output; and
indicator means, responsive to the ratio indicative output and calibrated to indicate component content, for indicating component content of said material.

24. A portable device for the measurement of a component content of a material according to claim 23, wherein said characteristic of microwave radiation is power of microwave radiation.

25. A portable device for the measurement of a component content of a material according to claim 16, wherein said attenuator means comprises a means for reducing microwave radiation power from said second output of said directional coupler means to a level substantially equal to microwave radiation power applied to said reference detector from said first output of said directional coupler means.

26. A portable device for the measurement of a component content of a material according to claim 16,
wherein said reference amplifier comprises:
a first preamplifier for providing a pre-amplified reference detector voltage output; and
a first amplifier, responsive to said pre-amplified reference detector voltage output, for providing an amplified reference detector voltage output to said logarithmic ratio amplifier means;
wherein said signal amplifier comprises:
a second preamplifier for providing a pre-amplified signal detector voltage output; and
a second amplifier, responsive to said pre-amplified signal detector voltage output, for providing an amplified signal detector voltage output to said logarithmic ratio amplifier means.

27. A portable device for the measurement of a component content of a material according to claim 25, wherein said microwave source means is comprised of a Gunn diode.

28. A portable device for the measurement of a component content of a material according to claim 25, wherein said indicator means is comprised of a digital voltmeter.

* * * * *